(12) United States Patent
Draper et al.

(10) Patent No.: US 8,632,671 B2
(45) Date of Patent: Jan. 21, 2014

(54) METHOD FOR MEASURING CARBON NANOTUBES TAKEN-UP BY A PLURALITY OF LIVING CELLS

(75) Inventors: Rockford K. Draper, Plano, TX (US); Paul Pantano, Plano, TX (US); Ru-Hung Wang, Dallas, TX (US); Carole Mikoryak, Richardson, TX (US)

(73) Assignee: Board of Regents, University of Texas System, Austin, TX (US)

( * ) Notice: Subject to any disclaimer, the term of this patent is extended or adjusted under 35 U.S.C. 154(b) by 251 days.

(21) Appl. No.: 13/121,395

(22) PCT Filed: Oct. 2, 2009

(86) PCT No.: PCT/US2009/059450
§ 371 (c)(1),
(2), (4) Date: May 12, 2011

(87) PCT Pub. No.: WO2010/040108
PCT Pub. Date: Apr. 8, 2010

(65) Prior Publication Data
US 2011/0203927 A1    Aug. 25, 2011

Related U.S. Application Data

(60) Provisional application No. 61/102,755, filed on Oct. 3, 2008.

(51) Int. Cl.
*G01N 27/447*    (2006.01)
(52) U.S. Cl.
USPC .......................................... 204/456; 204/466
(58) Field of Classification Search
USPC ......... 204/455, 456, 457, 459, 466, 467, 605, 204/610, 616–618
See application file for complete search history.

(56) References Cited

U.S. PATENT DOCUMENTS

| 4,389,670 A | 6/1983 | Davidson et al. |
| 5,541,255 A * | 7/1996 | Kozulic ....................... 525/54.3 |
| 5,717,602 A | 2/1998 | Kenning |
| 6,673,631 B1 * | 1/2004 | Tereba et al. ................. 436/526 |
| 2006/0191792 A1 | 8/2006 | Herr et al. |

FOREIGN PATENT DOCUMENTS

WO    2007075325 A2    7/2007

OTHER PUBLICATIONS

Heller et al. "Concomitant Length and Diameter Separation of Single-Walled Carbon Nanotubes," J. Am. Chem. Soc. 2004, 126, 14567-14573.*
Vetcher et al., "Electrophoretic Fractionation of Carbon Dispersions on Agarose Gels," International Journal of Nanoscience, vol. 6, No. 1 (2007) 1-7 published Feb. 2007.*

(Continued)

*Primary Examiner* — Alex Noguerola
(74) *Attorney, Agent, or Firm* — Edwin S. Flores; Chainey P. Singleton; Chalker Flores, LLP (57) ABSTRACT

The present invention provides methods, apparatuses and kits for determining the presence and the concentration of nanoparticles in a given area, solution or region via cellular uptake and/or adsorption monitored through laboratory equipment. For example, the present invention provides a method of quantifying one or more nanoparticles by incubating a nanoparticle solution comprising one or more nanoparticles with one or more cells; isolating the one or more cells; lysing the one or more cells to release a cell lysate; separating the cell lysate electrophoretically on a gel; digitizing the gel to form a gel image; quantifying the nanoparticle intensity in the gel image; and correlating the nanoparticle intensity to a cell-associated nanoparticle concentration.

8 Claims, 5 Drawing Sheets

(56) References Cited

OTHER PUBLICATIONS

Gao et al. "Carbon Nanotube Delivery of the GFP Gene into Mammalian Cells," ChemBioChem 2006, 7, 239-242 ("Gao") in view of Tereba et al. US 6,673,631 B1.*

Wei-Lung et al. "Using Nile Red-Adsorbed Gold Nanoparticles to Locate Glutathione within Erythrocytes," Langmuir 2005, 21, 10676-10683.*

Xiao et al. "Analysis of oxidized multi-walled carbon nanotubes in single K562 cells by capillary electrophoresis with laser-induced fluorescence," Anal. Bioanl. Chem (2007) 387:119-126 published Jul. 29, 2006.*

Hjerten, S (1985) J. Chromatogr 347:191-198.*

Bishit et al. "Polymeric nanoparticle-encapsulated curcumin ("nanocurcumin"): a novel strategy for human cancer therapy," Journal of Nanobiotechnology 2007, 5:3, pp. 1-8 (online journal, page numbers not for citation purposes).*

A recipe for forming agarose for gel electrophoresis from the GeneON products listing for Molecular Biology entitled "Agarose for gel-electrophoresis" downloaded on Jul. 12, 2013 from http://www.taq-dna.com/agarose-for-gel-electrophoresis-print199.html—copyright GeneOn Oct. 2007.*

Product description of SeaKem LE Agarose published by Lonza Rockland, Inc. 2007.*

* cited by examiner

METHOD FOR MEASURING CARBON NANOTUBES TAKEN-UP BY A PLURALITY OF LIVING CELLS

CROSS-REFERENCE TO RELATED APPLICATIONS

This application claims priority to U.S. Provisional Application Ser. No. 61/102,755 filed Oct. 3, 2008, the contents of which is incorporated by reference herein in its entirety.

STATEMENT OF FEDERALLY FUNDED RESEARCH

This invention was made with U.S. Government support under Contract No. W81XWH-07-1-0492 awarded by the United States Army Medical Research Acquisition Activity. The government has certain rights in this invention.

TECHNICAL FIELD OF THE INVENTION

The present invention relates in general to the field of quantification and detection of nanoparticles (e.g., fullerenes, nanotubes, nanowires, nanospheres and nanorods) in a sample.

BACKGROUND OF THE INVENTION

Without limiting the scope of the invention, its background is described in connection with nanoparticle detection, separation and quantification.

For example, single-wall carbon nanotubes (buckytubes) have unique properties, including high strength, stiffness, thermal and electrical conductivity. Generally, single-wall carbon nanotubes are hollow, tubular fullerene molecules consisting essentially of carbon atoms typically arranged in hexagons and pentagons. Single-wall carbon nanotubes typically have diameters in the range of about 0.5 nanometers to about 9.5 nm, and lengths usually greater than about 50 nm. Background information on single-wall carbon nanotubes can be found in U.S. Pat. No. 7,074,310. Although carbon nanotubes can be created, they are currently difficult to detect or analyze inside and/or adsorbed to cells. In addition, current methodologies are not suited to analyze a large population of cells in a timely fashion and/or they require the attachment of a reporter label to the carbon nanotubes.

SUMMARY OF THE INVENTION

The present invention provides methods, apparatuses and kits for determining the presence and the concentration of nanoparticles in a given area, solution or region via cellular uptake and/or adsorption monitored through laboratory equipment. For example, the present invention provides a method of quantifying one or more nanoparticles by incubating a nanoparticle solution comprising one or more nanoparticles with one or more cells; isolating the one or more cells; lysing the one or more cells to release a cell lysate; separating the cell lysate electrophoretically on a gel; digitizing the gel to form a gel image; quantifying the nanoparticle intensity in the gel image; and correlating the nanoparticle intensity to a cell-associated nanoparticle concentration.

The present invention includes a method of quantifying one or more nanoparticles by lysing one or more cells thought to contain one or more nanoparticles, releasing them into a cell lysate; separating the cell lysate electrophoretically on a gel; digitizing the gel to form a gel image; quantifying a nanoparticle intensity of one or more regions in the gel image; and correlating the nanoparticle intensity to a nanoparticle concentration.

A method is provided for quantifying one or more carbon nanotubes by incubating a nanotube solution with one or more cells; isolating the one or more cells; lysing the one or more cells to release a cell lysate; separating the cell lysate electrophoretically on a gel; digitizing the gel to form a gel image; quantifying a band intensity in the gel image; and correlating the band intensity to a nanotube concentration, wherein the nanotube concentration comprises metallic nanotubes, semi-conducting nanotubes or both. The present invention includes a method of quantifying one or more carbon nanotubes by lysing one or more cells thought to contain one or more nanotubes, releasing them into a cell lysate; separating the cell lysate electrophoretically on a gel; digitizing the gel to form a gel image; quantifying a nanotube intensity of one or more regions in the gel image; and correlating the nanotube intensity to a nanotube concentration, wherein the nanotube concentration comprises metallic nanotubes, semi-conducting nanotubes or both.

The present invention also includes a method of isolating one or more nanoparticles. The method includes incubating a nanoparticle solution comprising one or more nanoparticles with one or more cells; isolating the one or more cells; lysing the one or more cells to release a cell lysate; separating the cell lysate electrophoretically on a gel; digitizing the gel to form a gel image; quantifying the nanoparticle intensity in the gel image; and correlating the nanoparticle intensity to a nanoparticle concentration. The present invention also includes a method of isolating one or more carbon nanotubes. The method includes incubating a nanotube solution comprising one or more nanotube with one or more cells; isolating the one or more cells; lysing the one or more cells to release a cell lysate; separating the cell lysate electrophoretically on a gel; digitizing the gel to form a gel image; quantifying the nanotube intensity in the gel image; and correlating the nanotube intensity to a nanotube concentration, wherein the nanotube concentration comprises metallic nanotubes, semi-conducting nanotubes or both.

A label-free method is provided for quantifying one or more nanoparticles by separating the sample electrophoretically on a gel; digitizing the gel to form a gel image; quantifying a band intensity in the gel image; and correlating the band intensity to a nanoparticle concentration. A label-free method is provided for quantifying one or more carbon nanotubes by separating the sample electrophoretically on a gel; digitizing the gel to form a gel image; quantifying a band intensity in the gel image; and correlating the band intensity to a nanotube concentration, wherein the nanotube concentration comprises metallic nanotubes, semi-conducting nanotubes or both.

Furthermore the present invention includes a method of determining the uptake and/or adsorption of nanoparticles by a cell (i.e., cell-associated nanoparticles) by incubating a nanoparticle solution comprising one or more nanoparticles with one or more cells; isolating the one or more cells; lysing the one or more cells to release a cell lysate; separating the cell lysate electrophoretically on a gel; digitizing the gel to form a gel image; quantifying the nanoparticle intensity in the gel image; and correlating the nanoparticle intensity to a cell-associated nanoparticle concentration. Furthermore, the present invention includes a method of determining the uptake and/or adsorption of carbon nanotubes by a cell by incubating a nanotube solution comprising one or more nanotubes with one or more cells; isolating the one or more cells; lysing the one or more cells to release a cell lysate; separating the cell lysate electrophoretically on a gel; digitizing the gel to form a gel image; quantifying the nanotube intensity in the gel image; and correlating the nanotube intensity to a cell-associated nanotube concentration.

A method of determining a dosage of a nanoparticle active agent is also provided. Specifically, the method includes incubating a nanoparticle solution comprising one or more nanoparticles and one or more active agents with one or more cells; isolating the one or more cells; lysing the one or more cells to release a cell lysate; separating the cell lysate electrophoretically on a gel; digitizing the gel to form a gel image; quantifying the nanoparticle intensity in the gel image; and correlating the nanoparticle intensity to a concentration of the one or more active agents, wherein the concentration of the active agent in the one or more cells correlates to the dosage.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention provides methods, apparatuses and kits for determining the presence and the concentration of nanoparticles in a given area, solution or region via cellular uptake and/or adsorption monitored through laboratory equipment. For example, the present invention provides a method of quantifying one or more nanoparticles by incubating a nanoparticle solution comprising one or more nanoparticles with one or more cells; isolating the one or more cells; lysing the one or more cells to release a cell lysate; separating the cell lysate electrophoretically on a gel; digitizing the gel to form a gel image; quantifying the nanoparticle intensity in the gel image; and correlating the nanoparticle intensity to a cell-associated nanoparticle concentration.

The present invention provides that the one or more nanoparticles may include any nano-structure, e.g., fullerenes, quantum dots, inorganic nanospheres, metallic nanospheres, nanorods, carbon nanotubes, Si-nanotubes, nanowires, single-wall nanotubes, multi-wall nanotubes and combinations thereof. The one or more nanoparticles are in combination with one or more proteins, or protein coated. One such protein is BSA; however, the skilled artisan knows that other proteins, peptides, polymers, biolytes, and active agents may be used.

In addition the present invention includes a kit to quantify the concentration of one or more nanoparticles. The kit includes one or more cells for incubating a nanoparticle solution with one or more cells; and isolating the one or more cells. The kit includes one or more reagents for lysing the one or more cells to release a cell lysate. The kit includes one or more reagents for the preparation of a gel for separating the cell lysate electrophoretically. The kit includes instructions for digitizing the gel to form a gel image; and quantifying the nanoparticle intensity in the gel image; and correlating the nanoparticle intensity to a cell-associated nanoparticle concentration.

The present invention relates to fullerene tubes produced in carbon deposits on the cathode in carbon arc methods of producing spheroidal fullerenes from vaporized carbon. Ebbesen et al., "Large-Scale Synthesis Of Carbon Nanotubes," Nature, Vol. 358, p. 220 (Jul. 16, 1992) and Ebbesen et al., "Carbon Nanotubes," Annual Review of Materials Science, Vol. 24, p. 235 (1994). The present invention also relates to single-wall carbon nanotubes formed by the catalytic decomposition of carbon monoxide on bimetallic Co—Mo catalysts. See Kitiyanan et al., "Controlled Production of Single-Wall Carbon Nanotubes formed by the Catalytic Decomposition of CO on Bimetallic Co-Mo Catalysts," Chem. Phys. Lett., Vol 317, p. 497 (2000). The present invention also relates to single-wall carbon nanotubes formed in a DC arc discharge apparatus of the type used in fullerene production by simultaneously evaporating carbon and a small percentage of Group VIII transition metal from the anode of the arc discharge apparatus. See Tijima et al., "Single-Shell Carbon Nanotubes of 1 nm Diameter;" Nature, Vol. 363, p. 603 (1993); Bethune et al., "Cobalt Catalyzed Growth of Carbon Nanotubes with Single Atomic Layer Walls," Nature, Vol. 63, p. 605 (1993); Ajayan et al., "Growth Morphologies During Cobalt Catalyzed Single-Shell Carbon Nanotube Synthesis," Chem. Phys. Lett., Vol. 215, p. 509 (1993); Zhou et al., "Single-Walled Carbon Nanotubes Growing Radially From $YC_2$, Particles," Appl. Phys. Lett., Vol. 65, p. 1593 (1994); Seraphin et al., "Single-Walled Tubes and Encapsulation of Nanocrystals Into Carbon Clusters," Electrochem. Soc., Vol. 142, p. 290 (1995); Saito et al., "Carbon Nanocapsules Encaging Metals and Carbides," J. Phys., Chem. Solids, Vol. 54, p. 1849 (1993); Saito et al., "Extrusion of Single-Wall Carbon Nanotubes Via Formation of Small Particles Condensed Near an Evaporation Source," Chem. Phys. Lett., Vol. 236, p. 419 (1995). It is also known that the use of mixtures of such transition metals can significantly enhance the yield of single-wall carbon nanotubes in the arc discharge apparatus. See Lambert et al., "Improving Conditions Toward Isolating Single-Shell Carbon Nanotubes," Chem. Phys. Lett., Vol. 226, p. 364 (1994). Generally, the skilled artisan understands there are numerous methods of producing nanotubes, e.g., U.S. Pat. No. 7,074,310. The contents of all of which are incorporated by reference herein.

As used herein, SWNT is used to denote any single-wall carbon nanotube which are hollow, tubular fullerene molecules have unique properties, including high strength, stiffness, thermal and electrical conductivity.

The present invention provides analytical methods for identifying nanomaterials in biological systems. The present invention allows the quantification of nanomaterials and is particularly relevant to almost all biomedical applications of CNTs to living cells, ranging from intracellular sensors to chemotherapeutic agents and any other application dependent on the number of CNTs that are taken up by and/or adsorbed to cells. Statistically meaningful measures of the amounts of CNTs inside and/or adsorbed to cells are therefore required to evaluate the effectiveness of these applications. In contrast to current methods of detecting CNTs inside and/or adsorbed to cells, the present invention allows the detection of both metallic and semi-conducting CNT structures, can analyze CNTs in and/or adsorbed to living cells, is suited to analyze a large population of cells in a timely fashion, and does not require the attachment of a reporter label to the CNT. The present invention represents the first rapid, affordable method that can serve this purpose.

The present invention provides an analytical method that provides a rapid, inexpensive, label-free measurement of the concentration of all carbon nanotube (CNT) structures in a liquid sample. In one embodiment, the method requires only a gel-electrophoresis unit, a flatbed scanner, and basic image analysis software.

The present invention can be used to determine how many CNTs are taken up by and/or adsorbed to living cells. The present invention can be used to determine CNT concentrations from any biological matrix, any industrial process or waste stream. Furthermore, the invention is not limited to the detection of nanotubes; it should find applicability in determining the concentration of any nanoparticle type (e.g., fullerenes, quantum dots, inorganic or metallic nanospheres and nanorods, etc.) present in a liquid sample.

Figure 1:
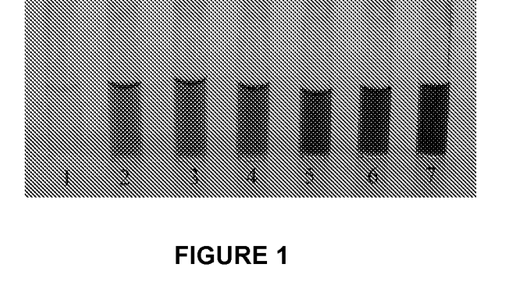
FIG. 1 is a photograph of vials containing different concentrations of CoMoCAT SWNT dispersions prepared in aqueous BSA solutions, and a BSA solution without SWNTs.

Preparation and characterization of the dispersed SWNT sample. For cell uptake studies, various concentrations of bovine serum albumin (BSA)-coated SWNTs were prepared by sonicating (10 minutes at 0° C. with a tip sonicator, 10W) 1 mg of SWNTs (CoMoCAT, from Southwest Nanotechnologies, Inc.) in 1 mL of various concentrations of aqueous BSA. Each dispersion was centrifuged once at 16,000×g for 2 minutes, the supernatant removed, and centrifuged again for 2 minutes at the same speed. The final supernatants (i.e., BSA-SWNTs) were very dark, indicating dispersion of the black SWNTs. FIG. 1 is a photograph of vials containing CoMoCAT SWNT dispersions prepared in aqueous BSA solutions. The concentration of BSA varied from (1) 0 mg/mL of BSA, (2) 12.5 mg/mL of BSA, (3) 25 mg/mL of BSA, (4) 50 mg/mL of BSA, (5) 100 mg/mL of BSA, (6) 150 mg/mL of BSA, to (7) 200 mg/mL of BSA.

Figure 2:
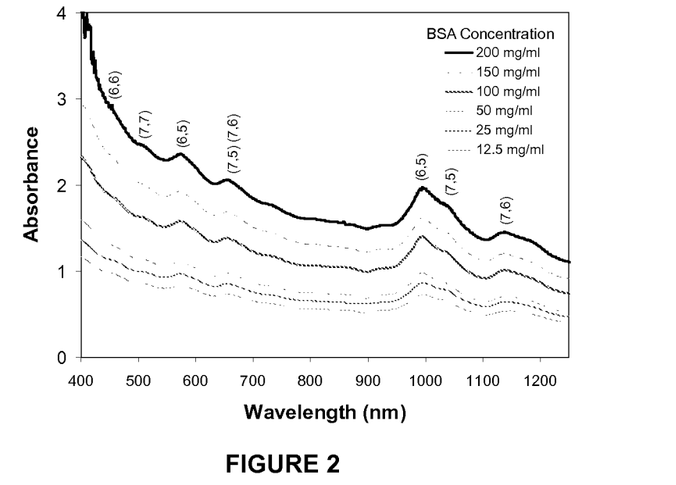
FIG. 2 is a graph of the background-corrected absorption spectrum of the CoMoCAT BSA-SWNT dispersions shown in FIG. 1.

FIG. 2 is an image of the background-corrected absorption spectrum of the CoMoCAT BSA-SWNT dispersions shown in FIG. 1. The main metallic and semi-conducting SWNT structures are denoted by their (n,m) chiral indices. The absorption spectra of the BSA-SWNT dispersions shown in FIG. 2 indicate that SWNTs dispersed in BSA retain their optical transitions between van Hove singularities in the electronic density of states, and that the concentration of the debundled SWNTs increases with increasing BSA concentrations (correlation coefficient=0.9925). Elemental analysis of BSA-SWNTs found background levels of molybdenum and cobalt, catalysts used in making this type of SWNT, indicating that >99% of these contaminants were removed by the dispersion preparation protocol.

Figure 3:
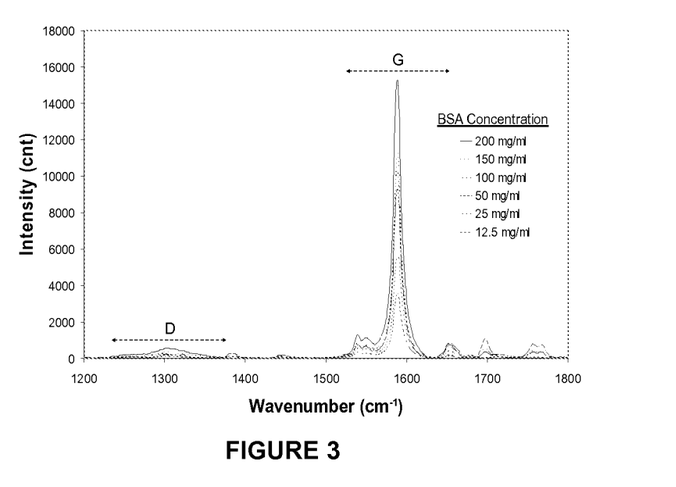
FIG. 3 is a graph of the Raman spectra acquired from CoMoCAT BSA-SWNT dispersions prepared in BSA solutions of various concentrations.

BSA-SWNTs were further characterized using Raman spectroscopy, which revealed a strong "G" line in the 1550-1610 cm−1 region, and other lines typical for SWNTs. FIG. 3 is graph of the Raman spectra (e.g., 633 nm laser excitation) acquired from CoMoCAT BSA-SWNT dispersions prepared in BSA solutions of various concentrations; all spectra were normalized to the same intensity scale. SWNTs in the dispersions increased with increasing BSA concentrations, indicated by the increasing "G" line intensities (correlation coefficient=0.9232). Control samples of BSA without SWNTs did not display detectable resonances under these operating conditions (data not shown).

Detection of SWNTs in BSA-SWNT samples by SDS-PAGE gel electrophoresis. The BSA-SWNT dispersions characterized above were analyzed by SDS-PAGE gel electrophoresis to demonstrate the linearity and specificity of the invention. As shown in FIG. 4, individual BSA-SWNT dispersions were run in separate lanes of a conventional SDS polyacrylamide gel. In brief, both proteins and SWNTs bind SDS and migrate towards the cathode because they have a negative charge from the sulfate on the SDS. Unexpectedly, however, the SWNTs accumulate in a band at the bottom of the sample loading wells. The accumulation of the black SWNTs at this interface also considerably concentrates the SWNTs, which increases the sensitivity of detection.

Figure 4A:
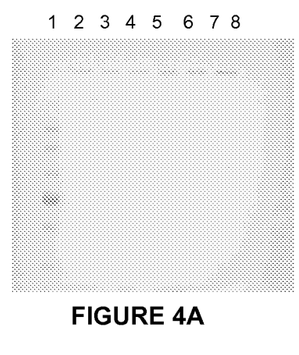
FIGS. 4A and 4B are images of SDS-PAGE gels of BSA-SWNTs.
Figure 4B:
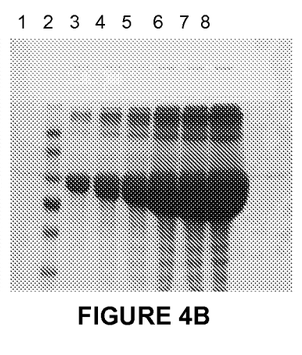

FIGS. 4A and 4B are images of SDS-PAGE gel electrophoresis of BSA-SWNTs and controls at 100 V for 2 hours. FIGS. 4A and 4B demonstrate separation of SWNTs from protein components after electrophoresis using digital scans of a 4% stacking 10% resolving 1.5 mm thickness mini gel as seen in FIG. 4A before and after as seen in FIG. 4B where the proteins were stained with 0.5% Commassie Blue. As seen in FIGS. 4A and 4B: Lane (1) is blank; lane (2) is pre-stained protein molecular weight markers; lanes (3) to (8) are 1 uL of SWNT dispersions prepared in various BSA concentrations: (3) 12.5 mg/mL, (4) 25 mg/mL, (5) 50 mg/mL, (6) 100 mg/mL, (7) 150 mg/mL, (8) 200 mg/mL.

Figure 5A:
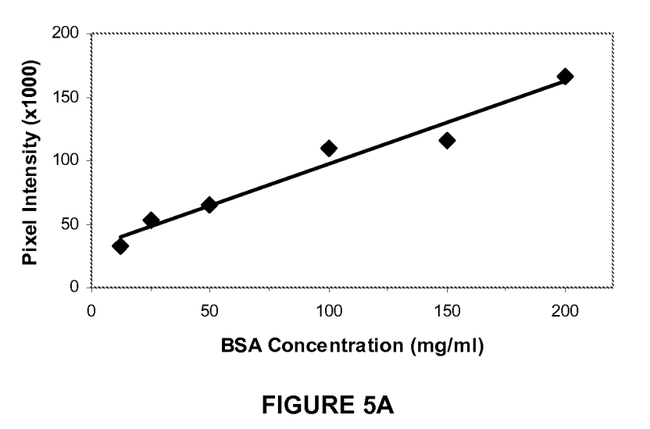
FIG. 5A is a graph of the pixel intensities of the digital gel image and FIG. 5B is the Raman spectra of SWNT gel bands after electrophoresis in a SDS-PAGE gel.

The black SWNTs are quantified at the interface after scanning the gel with a digital imager, followed by measuring the pixel intensities of the bands with IMAGEQUANT software. FIG. 5A shows the pixel intensities of the 6 dark bands shown in the top row of the gel shown in FIG. 4A. FIG. 5A is a graph comparing the pixel intensities of the digital image. The band intensities demonstrate that the signal is directly proportional to the material applied to the gel (correlation coefficient=0.9625) and that the signal is linear with concentration over a 20-fold range.

Figure 5B:
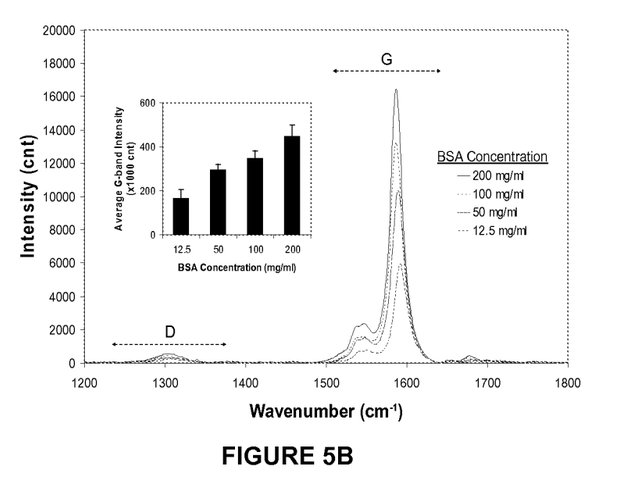

FIG. 5B is an image of the Raman spectra of SWNT bands after electrophoresis in a SDS-PAGE gel as a function of BSA concentration used to prepare the BSA-SWNT dispersions. When the dark bands were scanned using the Raman microprobe, prominent G lines are observed, demonstrating that the material in the bands are SWNTs. Additionally, the insert in FIG. 5B shows the linearity of G-line intensities from the various BSA-SWNT dispersions (correlation coefficient=0.9766) agree favorably with those determined by the gel electrophoresis/scanner detection method.

Figure 6:
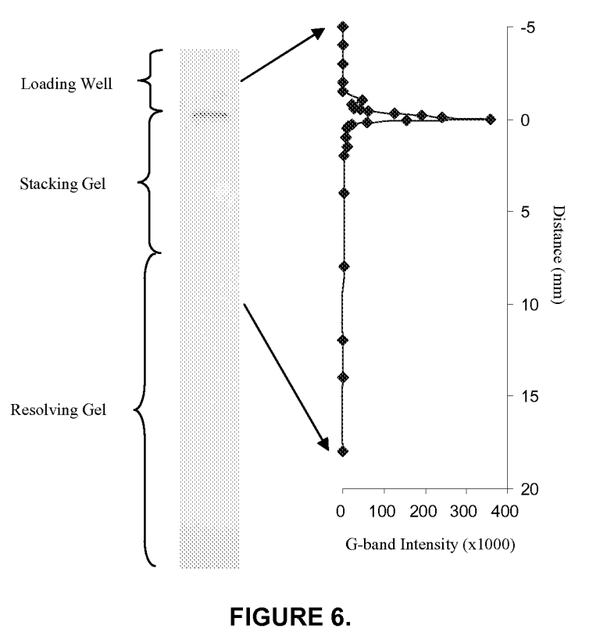
FIG. 6 is an image of Raman spectra G-line intensities as a function of distance above and below the bottom of the sample loading well within a lane of a SDS-PAGE gel.

FIG. 6 is an image of a lane of a SDS-PAGE gel and the Raman spectra G-line intensities as a function of distance from the bottom of the sample loading well. Each G-line intensity was calculated by integrating the intensities in the 1510 to 1630 $cm^{-1}$ region. Further evidence demonstrating that the dark material observed in the dark bands is SWNTs is provided by a series of studies whereby multiple regions above and below the interface of the gel were analyzed by microprobe Raman spectroscopy with about 5 μm lateral resolution. In these studies, the 633-nm laser beam excitation was first focused on the center of the SWNT band near the bottom of the well. As shown in FIG. 6, spectra were acquired from this region and at various spots along the length of the lane, above and below the SWNT band. The resulting vertical profile of G-line intensities clearly indicates that SWNT material is detected only in the band at the interface of the sample loading well and stacking gel.

Raman measurements of the uptake of SWNTs by living cells. The following section briefly reviews our published work on measuring the uptake of peptide- and protein-coated SWNTs by cells, [Chin et al., "Amphiphilic Helical Peptide Enhances the Uptake of Single-Walled Carbon Nanotubes by Living Cells," Exp. Biol. Med., Vol. 232, p 1236 (2007); Yehia et al., "Single-Walled Carbon Nanotube Interactions with HeLa Cells," J. Nanobiotechnol, Vol. 5, p 8 (2007)] (incorporated herein by reference) with the emphasis being on the designs and controls required to properly classify whether SWNTs are taken-up by cells.

Figure 7:
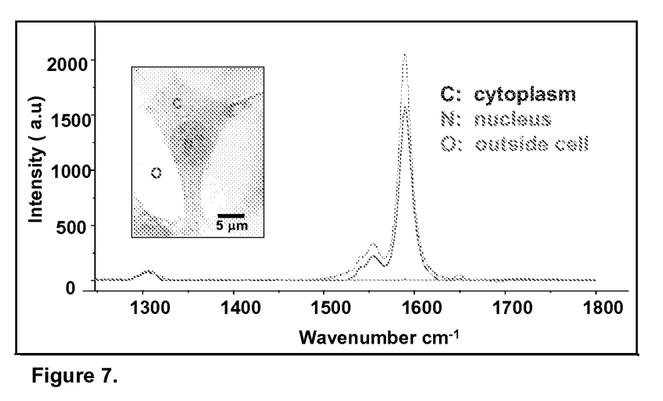
FIG. 7 is an image of a Raman spectra from a single HeLa cell following exposure to dispersed SWNTs.

HeLa cells were incubated at 37° C. for 22 hours in medium containing peptide-coated SWNTs. The cells were then washed extensively and analyzed by microprobe Raman spectroscopy to determine whether the SWNTs were inside cells by detection of their distinctive G-line signature at 1590 $cm^{-1}$. FIG. 7 shows typical results with one cell out of numerous cells that were analyzed. When the area probed was outside the cell, the Raman G line signal was negligible, but when either the cell cytoplasm or nuclear areas were probed, the signal was present at 1590 $cm^{-1}$ as seen in FIG. 7. Cells that were not exposed to SWNTs had no G line (data not shown). FIG. 7 is a Raman spectra from a single HeLa cell following exposure to dispersed SWNTs. The inset is a micrograph image of the cell studied showing the locations that were analyzed, e.g., the area outside the HeLa cell (O), the nucleus of the HeLa cell (N) and the cytoplasm (C) of the HeLa cell.

Figure 8:
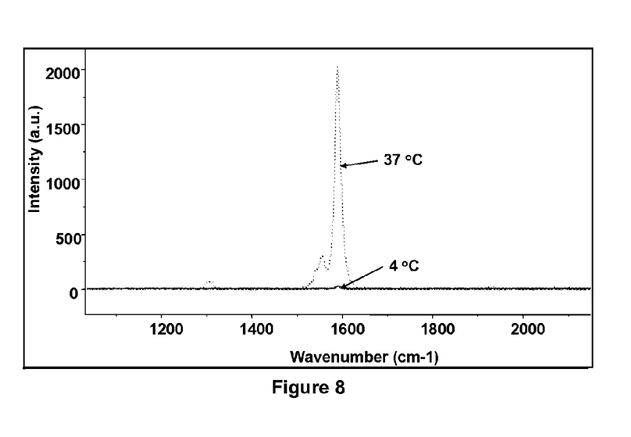
FIG. 8 is a graph of the Raman spectra of HeLa cells exposed to dispersed SWNTs.

The signal emanating from SWNT-treated cells could be from nanotubes inside the cells, or stuck to the exterior cell surface. If the signal was from inside the cells, most likely the result of active uptake, such as endocytosis, then the signal should be absent in cells exposed to the SWNTs at 4° C. where energy-dependent uptake ceases. FIG. 8 is a Raman spectra of HeLa cells exposed to dispersed SWNTs at either 37° C. or 4° C. FIG. 8 compares the Raman spectra from a cell exposed to SWNTs at 37° C. and 4° C. for 22 hours, washed extensively, and prepared for Raman microprobe analysis. There was essentially no SWNT signal from this cell, or others analyzed at 4° C., evidence that the Raman signal from cells exposed to SWNTs is from nanotubes that required metabolic activity to accumulate in cells. This result also shows that any SWNTs adhering to the outside of cells at 4° C. were washed away, arguing that the Raman signal from cells at 37° C. is due to nanotubes inside the cells, not adhering to the outside.

Figure 9A:
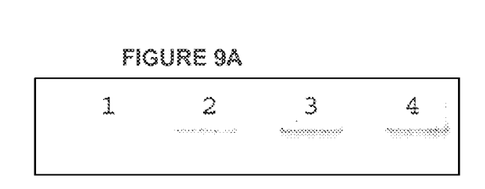
FIG. 9A is an image of the SWNT band region of the SDS-PAGE gel from cell lysates and control after electrophoresis.
Figure 9B:
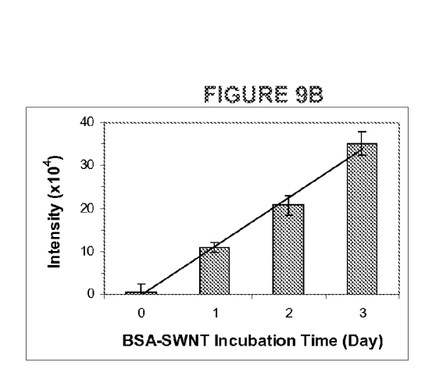
FIG. 9B is a graph of the relative pixel intensities of SWNT gel bands as indicative of SWNT content in cell lysates as a function of incubation time.
Figure 9C:
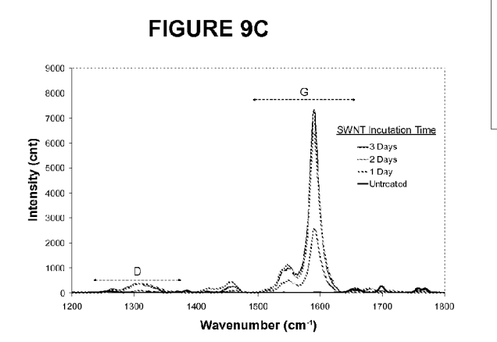
FIG. 9C is an image of Raman spectra acquired from the SWNT band region of the gel from cell lysates and control.

Normal rat kidney (NRK) cells in culture were incubated continuously for 1, 2, and 3 days in BSA-SWNT dispersions of the same concentration. FIG. 9A is a digital image of a SDS-PAGE gel showing the SWNT band region of the SDS-PAGE gel after electrophoresis. Lane (1) is a 3 day incubation in media that contains no SWNT dispersion; lanes (2) to (4) are cells incubated in media containing BSA-SWNT for 1, 2, or 3 days, respectively. FIG. 9B is a graph of the relative pixel intensity of SWNT band as indicative of SWNT content in cell lysates as a function of incubation time. The average and standard deviation values were determined from three independent studies. FIG. 9C is a Raman spectra acquired on the dried gel using a 50×objective with laser excitation at 633 nm focused on SWNT band areas. The representative spectra were obtained by merging three spectra acquired from the dark band area in each lane.

Figure 10A:
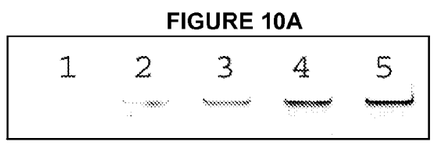
FIG. 10A is an image of the SWNT band region of the SDS-PAGE gel from cell lysates and control after electrophoresis.
Figure 10B:
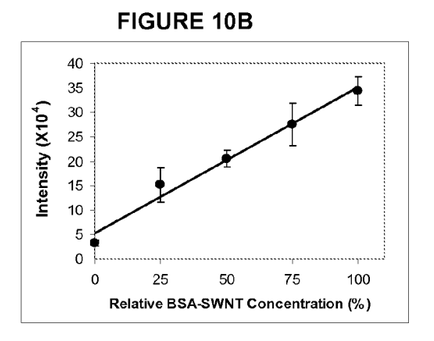
FIG. 10B is a graph of the relative pixel intensities of SWNT gel bands as indicative of SWNT content in cell lysates after 3 days uptake.

NRK cells in culture were incubated continuously for 3 days in BSA-SWNT dispersions of differing concentrations. FIG. 10A is a digital image of a SDS-PAGE gel that shows the SWNT band regions of the SDS-PAGE gel after electrophoresis. Lane (1) is control media contains no SWNT dispersion; lane (2) is 25% SWNT dispersion; lane (3) is 50% SWNT dispersion; lane (4) is 75% SWNT dispersion; lane (5) is media with undiluted (100%) SWNT dispersion. FIG. 10B is a graph of the relative pixel intensities of SWNT gel bands as indicative of SWNT content in cell lysates after 3 days uptake. The average and standard deviation values were determined from three independent trials. FIG. 10 shows that the amount of SWNTs taken up by NRK cells increases as a function of SWNT concentration in the BSA-SWNT dispersions (correlation coefficient=0.9811), and that no appreciable signal was generated for control cells not exposed to BSA-SWNTs.

Figure 11A:
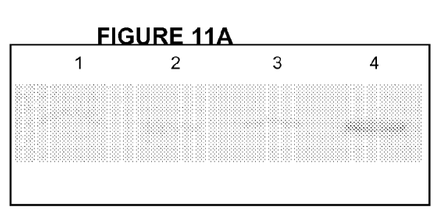
FIG. 11A is an image of the SWNT band region of the SDS-PAGE gel from cell lysates and control after electrophoresis.
Figure 11B:
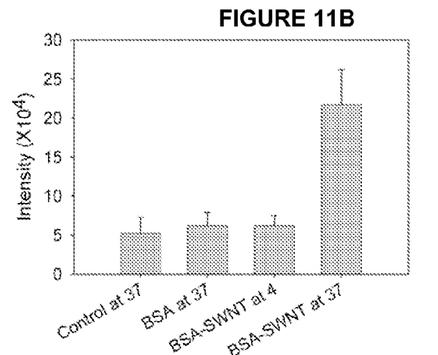
FIG. 11B is a graph of the relative pixel intensities of SWNT gel bands as indicative of SWNT content in cell lysate samples at various temperatures.

NRK cells in culture were incubated continuously for 1 day in BSA-SWNTs at a constant concentration but at two temperatures. FIG. 11 shows that there was essentially no SWNT signal from cells analyzed at 4° C. vs. cells analyzed at 37° C. This result suggests that any SWNTs adhering to the surface of cells were washed away, and that the SWNT signal detected is from SWNTs that accumulate inside cells, owing to the cellular metabolic activity that occurs at 37° C. but not at 4° C. FIG. 11A is a digital image of a SDS-PAGE gel that shows the SWNT band region of the SDS-PAGE gel after electrophoresis. Lane (1) is untreated control cells at 37° C.; lanes (2) to (4) are cells incubated in media contains (2) BSA at 37° C., (3) BSA-SWNT at 4° C., and (4) BSA-SWNT at 37° C. for 24 hours. FIG. 11B is a graph of the relative pixel intensities of SWNT gel bands as indicative of SWNT content in cell lysate samples. The average and standard deviation values were obtained from three independent trials.

Although the present invention is characterized using PAGE, the skilled artisan will readily understand that in addition to various gel percentages, other forms of separation may be used, any form of gel electrophoresis including multidimensional gel electrophoresis and capillary zone gel electrophoresis.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of quantifying one or more nanoparticles comprising the steps of:
    lysing one or more cells thought to comprise one or more nanoparticles to release a cell lysate;
    separating the cell lysate electrophoretically on a gel;
    digitizing the gel to form a gel image;
    quantifying a nanoparticle intensity of one or more regions in the gel image; and
    correlating the nanoparticle intensity to a cell-associated nanoparticle concentration.

2. The method of claim 1, wherein the one or more nanoparticles comprise fullerenes, quantum dots, inorganic nanospheres, metallic nanospheres, nanorods, carbon nanotubes, Si-nanotubes, nanowires, single-wall nanotubes, multi-wall nanotubes and combinations thereof.

3. A method of isolating one or more nanoparticles comprising the steps of:
    incubating a nanoparticle solution comprising one or more nanoparticles with one or more cells;
    isolating the one or more cells;
    lysing the one or more cells to release a cell lysate;
    separating the cell lysate electrophoretically on a gel;
    digitizing the gel to form a gel image; quantifying the nanoparticle intensity in the gel image; and
    correlating the nanoparticle intensity to a cell-associated nanoparticle concentration.

4. The method of claim 3, wherein the one or more nanoparticles comprise fullerenes, quantum dots, inorganic nanospheres, metallic nanospheres, nanorods, carbon nanotubes, nanowires, single-wall nanotubes, multi-wall nanotubes and combinations thereof.

5. A method of determining the uptake and/or adsorption of nanoparticles by a cell comprising the steps of:
    incubating a nanoparticle solution comprising one or more nanoparticles with one or more cells;
    isolating the one or more cells;
    lysing the one or more cells to release a cell lysate;
    separating the cell lysate electrophoretically on a gel;
    digitizing the gel to form a gel image;
    quantifying the nanoparticle intensity in the gel image; and
    correlating the nanoparticle intensity to a cell-associated nanoparticle concentration.

6. The method of claim 5, wherein the one or more nanoparticles comprise fullerenes, quantum dots, inorganic nanospheres, metallic nanospheres, nanorods, carbon nanotubes, Si-nanotubes, nanowires, single-wall nanotubes, multi-wall nanotubes and combinations thereof.

7. A method of determining a dosage of a nanoparticle active agent comprising the steps of:
    incubating a nanoparticle solution comprising one or more nanoparticles and one or more active agents with one or more cells;
    isolating the one or more cells;
    lysing the one or more cells to release a cell lysate;
    separating the cell lysate electrophoretically on a gel;
    digitizing the gel to form a gel image;
    quantifying the nanoparticle intensity in the gel image; and
    correlating the nanoparticle intensity to a concentration of the one or more active agents, wherein the concentration of the active agent in the one or more cells correlates to the dosage.

8. The method of claim 7, wherein the one or more nanoparticles comprise fullerenes, quantum dots, inorganic nanospheres, metallic nanospheres, nanorods, carbon nanotubes, Si-nanotubes, nanowires, single-wall nanotubes, multi-wall nanotubes and combinations thereof.

* * * * *